(12) United States Patent  
Neumann

(10) Patent No.: US 11,037,679 B1  
(45) Date of Patent: Jun. 15, 2021

(54) METHODS AND SYSTEMS OF BIOMETRIC IDENTIFICATION IN TELEMEDICINE USING REMOTE SENSING

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 16/939,408

(22) Filed: Jul. 27, 2020

(51) Int. Cl.
| | |
|---|---|
| G16H 40/67 | (2018.01) |
| G16H 80/00 | (2018.01) |
| H04L 29/06 | (2006.01) |
| G06K 9/62 | (2006.01) |
| G06K 9/00 | (2006.01) |

(52) U.S. Cl.
CPC ........... *G16H 40/67* (2018.01); *G06K 9/6215* (2013.01); *G06K 9/6256* (2013.01); *G16H 80/00* (2018.01); *H04L 63/0861* (2013.01); *G06K 9/00087* (2013.01); *G06K 9/00302* (2013.01); *G06K 9/00348* (2013.01); *G06K 9/00617* (2013.01); *G06K 9/00892* (2013.01); *G06K 2009/00932* (2013.01); *G06K 2009/00939* (2013.01)

(58) Field of Classification Search  
CPC combination set(s) only.  
See application file for complete search history.

(56) References Cited

U.S. PATENT DOCUMENTS

| | | | |
|---|---|---|---|
| 9,361,021 B2 | 6/2016 | Jordan et al. | |
| 9,980,644 B2 | 5/2018 | Fried et al. | |
| 10,216,906 B2 | 2/2019 | Desgranges et al. | |
| 10,325,070 B2 | 6/2019 | Beale et al. | |
| 10,586,020 B2 | 3/2020 | Madhavan et al. | |
| 2012/0029303 A1 | 2/2012 | Shaya | |

(Continued)

OTHER PUBLICATIONS https://www.researchgate.net/profile/Scott_Sittig/publication/335276477_Risk_Analysis_of_Residual_Protected_Health_Information_of_Android_Telehealth_Apps_Completed_Research_Full_Paper/links/5d5c30dd92851c37636e103a/Risk-Analysis-of-Residual-Protected-Health-Information-of-Android-Telehealth-Apps-Completed-Research-Full-Paper.pdf.
https://www.ncbi.nlm.nih.gov/pmc/articles/PMC5716614/pdf/ijt-09-3.pdf.

*Primary Examiner* — Michael Tomaszewski  
*Assistant Examiner* — William T. Monticello  
(74) *Attorney, Agent, or Firm* — Caldwell Intellectual Property Law, LLC

(57) ABSTRACT

In an aspect, a system for biometric identification in telemedicine using remote sensing, the system includes a computing device configured to initiate a communication interface between the computing device and a client device operated by a human subject, wherein the communication interface includes an audiovisual streaming protocol, receive, from at least a remote sensor at the human subject, a plurality of current physiological data, generate at least a biometric identification signature of the human subject, wherein generating further includes receiving subject signature training data, including a plurality of category descriptors and correlated physiological data entries, training a biometric signature model as a function of the subject signature training data and a machine-learning process, generating the biometric identification signature as a function of the biometric signature model, determining a degree of similarity between the plurality of current physiological data and the at least a biometric signature, and calculate an identity quantifier as a function of the degree of similarity.

20 Claims, 6 Drawing Sheets

(56) References Cited

U.S. PATENT DOCUMENTS

| | | | |
|---|---|---|---|
| 2015/0033305 A1* | 1/2015 | Shear et al. |
| 2015/0324692 A1* | 11/2015 | Ritchey et al. |
| 2016/0352727 A1* | 12/2016 | Day et al. |
| 2017/0011179 A1 | 1/2017 | Arshad et al. |
| 2017/0024537 A1 | 1/2017 | Ferlito |
| 2018/0012227 A1* | 1/2018 | Tunnell et al. |
| 2018/0212960 A1* | 7/2018 | Sandeep et al. |
| 2019/0027256 A1 | 1/2019 | Singh et al. |
| 2019/0384901 A1* | 12/2019 | Osborn et al. |
| 2019/0392145 A1* | 12/2019 | Komogortsev |

* cited by examiner

METHODS AND SYSTEMS OF BIOMETRIC IDENTIFICATION IN TELEMEDICINE USING REMOTE SENSING

FIELD OF THE INVENTION

The present invention generally relates to the field of security. In particular, the present invention is directed to methods and systems of biometric identification in telemedicine using remote sensing.

BACKGROUND

Network connections can be susceptible to attack, leading to publication of private and sensitive information. Frequently, this can leave users unable to securely communicate, particularly in situations in need of immediate attention.

SUMMARY OF THE DISCLOSURE

In an aspect, a system for biometric identification in telemedicine using remote sensing, the system includes a computing device configured to initiate a communication interface between the computing device and a client device operated by a human subject, wherein the communication interface includes an audiovisual streaming protocol, receive, from at least a remote sensor at the human subject, a plurality of current physiological data, generate at least a biometric identification signature of the human subject, wherein generating further includes receiving subject signature training data, including a plurality of category descriptors and correlated physiological data entries, training a biometric signature model as a function of the subject signature training data and a machine-learning process, generating the biometric identification signature as a function of the biometric signature model, determining a degree of similarity between the plurality of current physiological data and the at least a biometric signature, calculate an identity quantifier as a function of the degree of similarity, and provide the plurality of current physiological data to a user of the computing device using the communication interface as a function of the identity quantifier.

In another aspect, a method of biometric identification in telemedicine using remote sensing includes initiating, by a computing device, a communication interface between the computing device and a client device operated by a human subject, wherein the communication interface includes an audiovisual streaming protocol, receiving, by the computing device and from at least a remote sensor at the human subject, a plurality of current physiological data, generating, by the computing device, at least a biometric identification signature of the human subject, wherein generating further includes receiving subject signature training data, including a plurality of category descriptors and correlated physiological data entries, training a biometric signature model as a function of the subject signature training data and a machine-learning process, and generating the biometric identification signature as a function of the biometric signature module, determining, by the computing device, a degree of similarity between the plurality of current physiological data and the at least a biometric signature, calculating, by the computing device, an identity quantifier as a function of the degree of similarity, and providing the plurality of current physiological data to a user of the computing device using the communication interface as a function of the identity quantifier.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Embodiments described herein extract biometric signatures from human subject data and use the biometric signatures to authenticate remote sensor data. Remote sensor data may be used to authenticate concurrently received physiological data for use in telemedicine diagnostics, or may be used in its own right as such physiological data.

Figure 1:
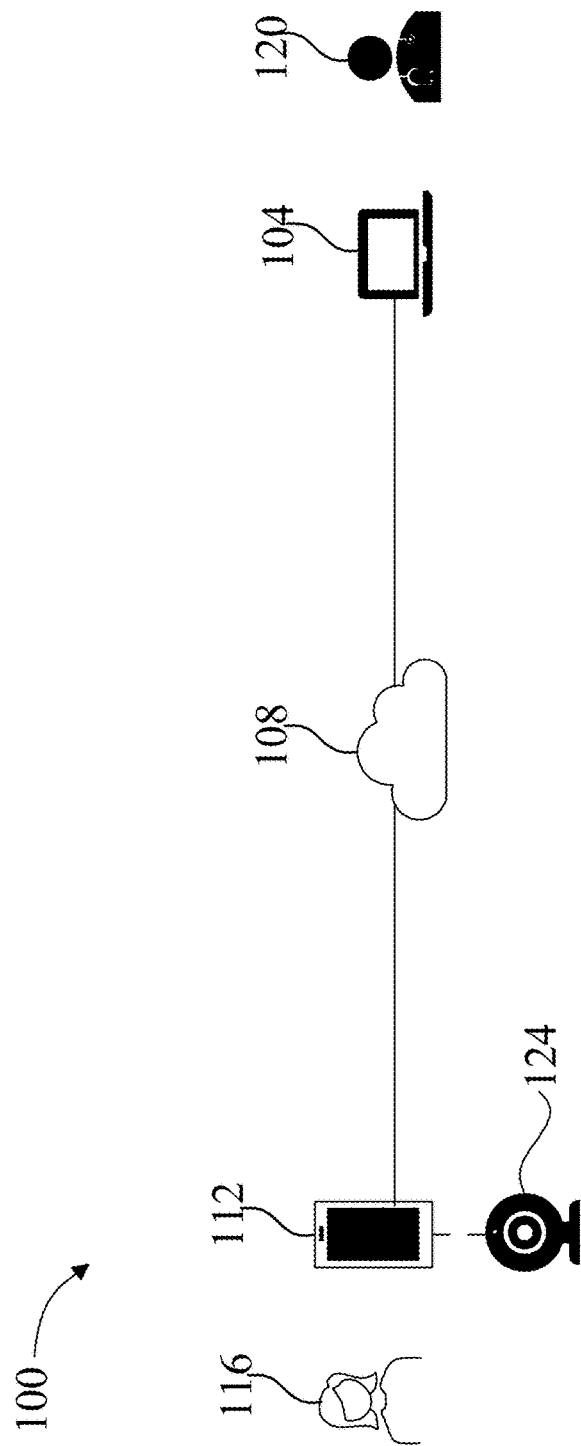
FIG. 1 is a schematic diagram of an exemplary embodiment of a system for biometric identification in telemedicine using remote sensing.

Referring now to FIG. 1, an exemplary embodiment of a system 100 for biometric identification in telemedicine using remote sensing is illustrated. System 100 includes a computing device 104. Computing device 104 may include any computing device as described in this disclosure, including without limitation a microcontroller, microprocessor, digital signal processor (DSP) and/or system 100 on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device 104 or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device 104 or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device 104, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device 104.

Computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 is configured to initiate a communication channel interface 108 between the computing device 104 and a client device 112 operated by a human subject 116. A "human subject," as used in this disclosure, is a person at a client device 112 receiving telemedicine services such as a virtual doctor's visit, physical, "checkup," or the like. A "communication channel interface," as used in this disclosure, is a communication medium within an interface. A communication channel interface 108 may include an application, script, and/or program capable of providing a means of communication between at least two parties, including any oral and/or written forms of communication. A communication channel interface 108 may allow computing device 104 to interface with electronic devices through graphical icons, audio indicators including primary notation, text-based user interfaces, typed command labels, text navigation, and the like. A communication channel interface 108 may include slides or other commands that may allow a user 120 to select one or more options. A communication channel interface 108 may include free form textual entries, where a user 120 may type in a response and/or message. A communication channel interface 108 includes a display interface. Display interface includes a form or other graphical element having display fields, where one or more elements of information may be displayed. Display interface may display data output fields including text, images, or the like containing one or more messages. A communication channel interface 108 may include data input fields such as text entry windows, drop-down lists, buttons, checkboxes, radio buttons, sliders, links, or any other data input interface that may capture user 120 interaction as may occur to persons skilled in the art upon reviewing the entirety of this disclosure. A communication channel interface 108 may be provided, without limitation, using a web browser, a native application, a mobile application, and the like.

With continued reference to FIG. 1, computing device 104 initiates a communication channel interface 108 with a client device 112. A "client device," as used in this disclosure, is a second computing device 104, including for example a mobile device such as a smartphone, tablet, laptop, desktop, and/or any other type of device suitable for use as computing device 104. Client device 112 is operated by a human subject 116; human subject 116 may include a person to whom telemedicine services are being rendered, including without limitation a patient. Computing device 104 may initiate communication channel interface 108 using any network methodology as described herein. In an embodiment, a communication channel interface 108 may be utilized to facilitate communications between a client device 112 operated by a human subject 116, and computing device 104 which may be operated by a user 120; user 120 may include a doctor, nurse, nurse practitioner, medical technician, medical assistant, pharmacist, pharmacy technician, and/or any other medical professional. For example, client device 112 may be operated by a patient who is in communication with a medical professional operating computing device 104, and communication channel interface 108 may be utilized to have a telemedicine appointment. In yet another non-limiting example, client device 112 may be operated by a first member of a support group, and computing device 104 may be operated by a second member of the support group, whereby communication channel interface 108 may be utilized to facilitate support group meetings and secure communications between members of the support group.

With continued reference to FIG. 1, a communication channel interface 108 includes an audiovisual capture device 124. An "audiovisual capture device," as used in this disclosure, is a device used to record sound and/or images. An audiovisual capture device 124 may include but is not limited to, a camera, a video camera, a mobile device, a recording device, a DVD player, a sensor, a television tuner, a video capture card, a universal serial bus (USB) audio and/or visual capture device, and the like. In an embodiment, an audiovisual capture device 124 may be located within client device 112.

Still referring to FIG. 1, communication interface includes an audiovisual streaming protocol. An "audiovisual streaming protocol," as used in this disclosure, is a packet-based communication protocol that streams video and/or audio data from one device to another and vice-versa. An audiovisual streaming protocol may support a "video chat" process whereby a user 120 of computer device can see real-time or near real-time footage of human subject 116, while human subject 116 may be able to see real-time or near real-time footage of user 120 of computing device 104. User 120 of computing device 104 may include, without limitation, a doctor, physician, nurse practitioner, nurse, therapist, psychologist, medical technician, and/or any other medical professional and/or assistant thereof. Audiovisual streaming protocol may enable user 120 to perform many actions of a medical visit virtually, for instance by having human subject 116 perform measurements of height and/or weight of human subject 116, by having human subject 116 present different body parts for inspection using audiovisual capture device 124, or the like.

Figure 2:
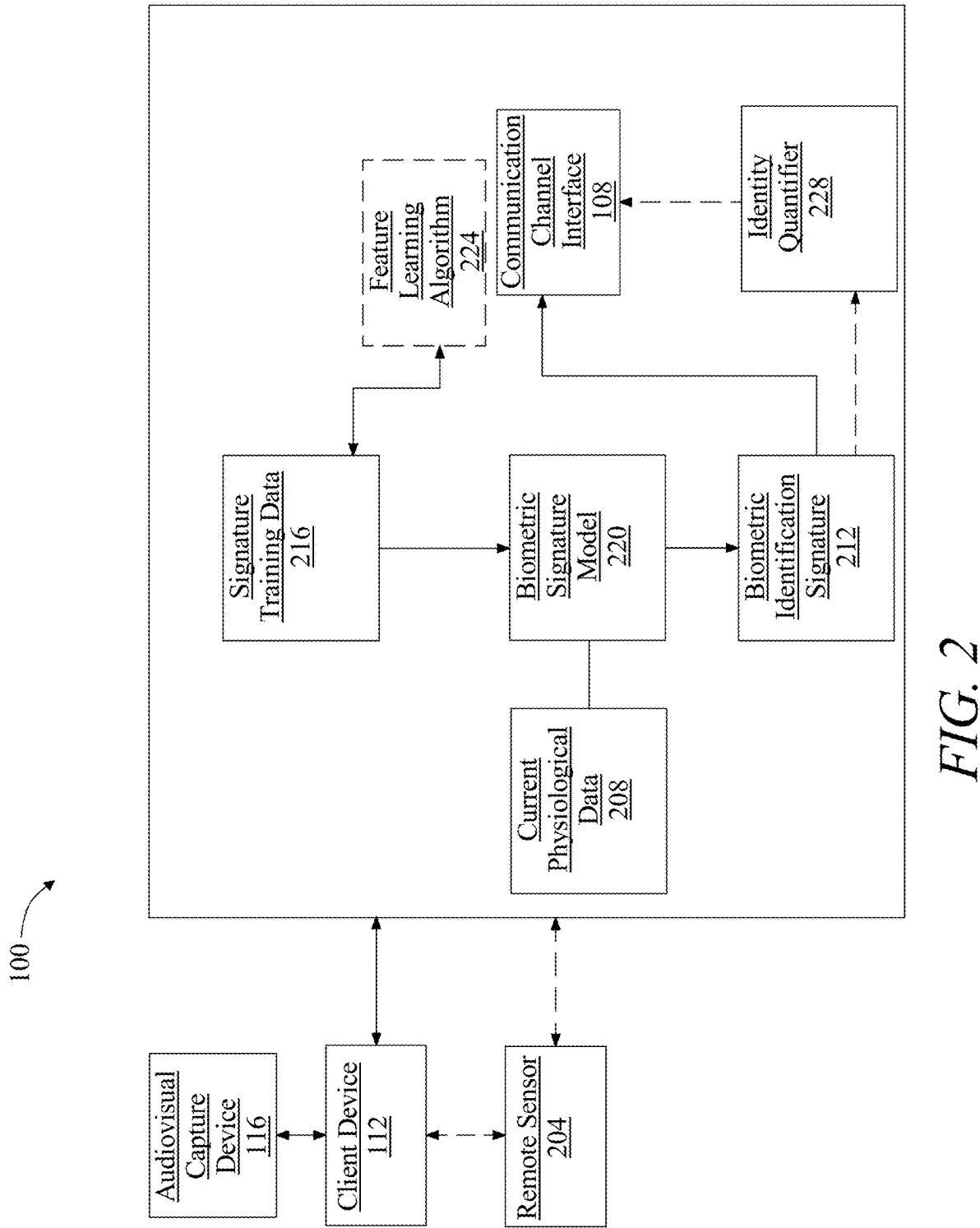
FIG. 2 is a block diagram of an exemplary embodiment of a system for biometric identification in telemedicine using remote sensing.

Referring now to FIG. 2, computing device 104 is configured to receive a plurality of current physiological data 208 from at least a remote sensor 204 at the human subject 116. A "remote sensor 204," as used in this disclosure, is a device that captures data of human subject 116 and transmits that data to computing device 104, either by transmitting the data to client device 112 which relays the data to computing device 104, or by transmitting the data separately over a network connection. Data may be transmitted via communication channel interface 108 and/or via a separate network connection formed, for instance, using a secure sockets layer (SSL) and/or hypertext transfer protocol-secure (HTTPS) process. Remote sensor 204 may include, without limitation, a camera such as a digital camera incorporated in a mobile device or the like, a microphone such as a mobile device microphone, a motion sensor, which may include one or more accelerometers, gyroscopes, magnetometer, or the like. Remote sensor 204 may include one or more peripheral devices such as a peripheral pulse oximeter or the like. Remote sensor 204 may include a network-connected device such as a network connected digital scale or the like. In an embodiment, remote sensor 204 may be used to capture audio or visual data concerning one or more portions of human subject 116's anatomy. For instance, and without limitation, a microphone may be pressed against one or more portions of human subject 116 at direction of user 120 over communication channel, causing capture of audio data from the one or more portion of human subject 116; as a non-limiting example, audio data of human subject 116 lungs, heart, digestive system 100, or the like may be so captured. As a further example, user 120 may instruct human subject 116 to train a camera on one or more portions of anatomy to capture visual data concerning such one or more portions. Such physiological data may be combined; for instance, audio capture of circulatory system 100 noise data may be combined with pulse oximetry data from a peripheral pulse oximeter and/or motion-sensor data indicating a degree of activity. Remote sensor 204 may include an electrical sensor such as a portable electrocardiogram device or the like. Generally, any sensor capable of capturing data of human subject 116 and transmitting such data locally or over a network may be used as a remote sensor 204.

Still referring to FIG. 2, plurality of current physiological data 208 may include cardiovascular data such as heart rate data, blood pressure data, or the like, for instance captured using audio and/or oximetry devices. Plurality of current physiological data 208 may include respiratory data such as audio capture of pulmonary sounds using a microphone or the like. Plurality of current physiological data 208 may include neurological data. Plurality of current physiological data 208 may include digestive audio data. Plurality of physiological data may include visual data captured regarding one or more elements of externally visible patient anatomy. Plurality of physiological data may capture one or more elements of human subject 116 bodily motion, including gait, posture or gestural motions.

Still referring to FIG. 2, computing device 104 is configured to generate at least a biometric identification signature of human subject 116. As used in this disclosure, a "biometric identification signature" is pattern of physiological data that is unique or nearly unique to human subject 116. "Nearly unique," as used in this disclosure, means that a probability of match to human subject 116, as opposed to another person, is very high; for instance, in an embodiment, a nearly unique biometric signature may be associated with a 95% or greater probability that a person evincing such a pattern is human subject 116 and not another person.

In an embodiment, at least a biometric identification signature 212 may include fingerprint data, such as a unique layout of 10-12 minutiae on user 120's fingerprint, uniquely identifying a user 120. A different user 120 may produce a different biometric pattern based on that user 120's layout of minutiae on a fingerprint. In yet another embodiment, at least a biometric identification signature 212 may include an iris scan consisting of unique rings, furrows, and freckles representing that user 120's iris. A different user 120 would trigger a different set of rings, furrows, and freckles and may ultimately produce least a biometric identification signature 212 representing that specific user 120's iris. In yet another embodiment, at least a biometric identification signature 212 may include a hand geometry scan consisting of shape, length, and width of the user 120's hand. In an embodiment, at least a biometric identification signature 212 may include a vein scan produced from a user 120's vein veins or other blood vessels such as human subject 116's a digital representation of patterns of blood vessels heading toward human subject 116's heart taken from human subject 116's wrist. In yet another embodiment, a face scan produced from a human subject 116's face may be used as at least a unique biometric identification signature 212. At least a biometric identification signature 212 may include a digital representation of user 120's size, position, and/or shape of eyes, nose, cheekbones, and jaw.

Still referring to FIG. 2, at least a biometric identification signature 212 may include one or more cardiovascular data such as heart rate at different activity levels. At least a biometric identification signature 212 may include one or more motion-related parameters such as gait, posture, gestural data, or the like. At least a biometric identification signature 212 may include facial feature data. At least a biometric identification signature 212 may include a combination of two or more of above-described elements such as without limitation a combination of gait and heart rate, gait, heart rate, and facial features, or the like. Combinations may be used, without limitation, to create a greater degree of accuracy in identifying a user 120 where sensor data lacks accuracy to identify a user 120 based on a single factor alone.

Figure 3:
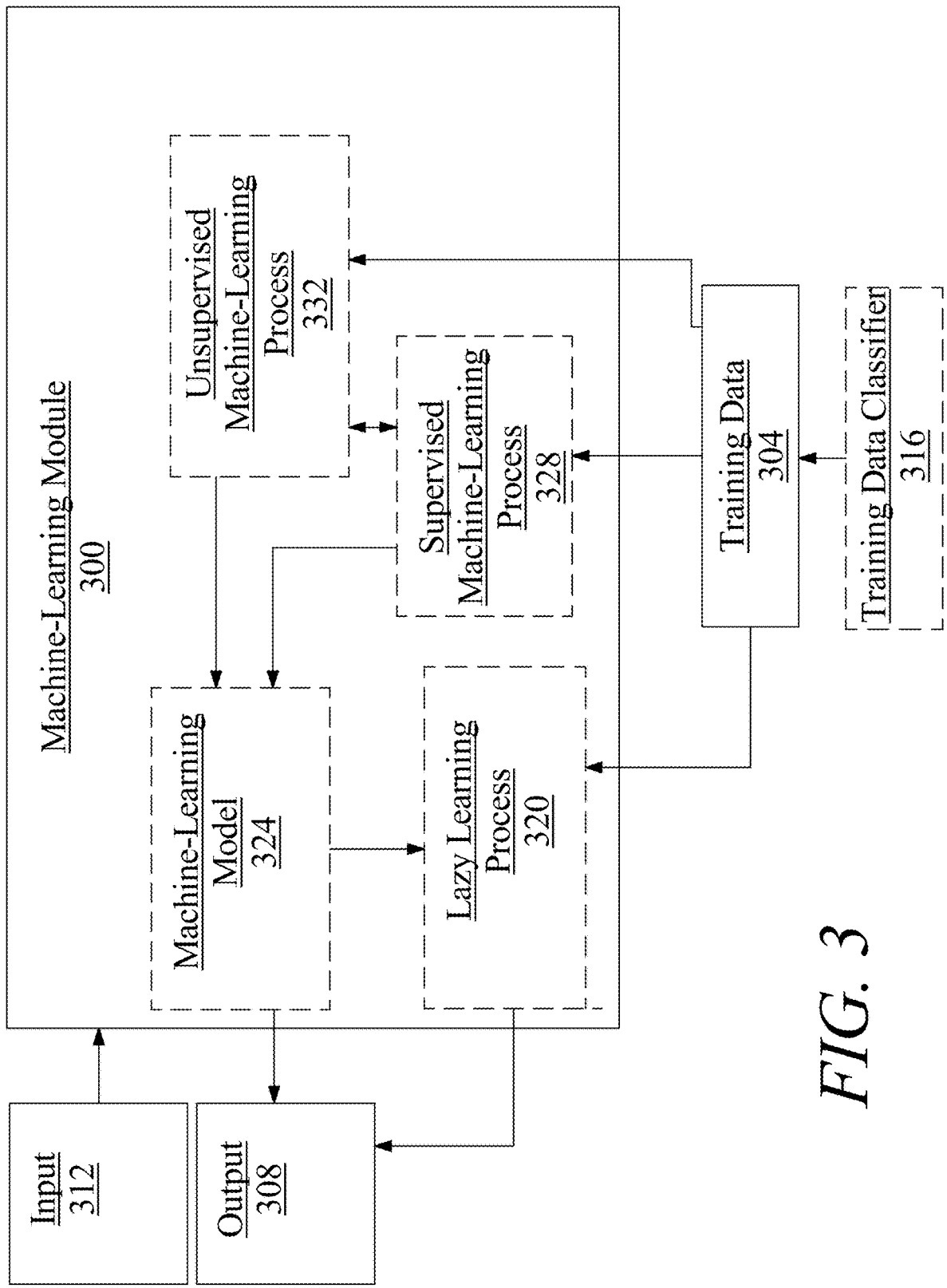
FIG. 3 is a block diagram of an exemplary embodiment of a machine-learning module.

Referring to FIG. 3, generation of biometric signature may be performed using a machine-learning process. Referring now to FIG. 3, an exemplary embodiment of a machine-learning module 300 that may perform one or more machine-learning processes as described in this disclosure is illustrated. Machine-learning module may include any suitable Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm that will be performed by a computing device 104/module to produce outputs 308 given data provided as inputs 312; this is in contrast to a non-machine learning software program where the commands to be executed are determined in advance by a user 120 and written in a programming language.

Still referring to FIG. 3, "training data," as used herein, is data containing correlations that a machine-learning process may use to model relationships between two or more categories of data elements. For instance, and without limitation, training data 304 may include a plurality of data entries, each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 300 may generate a classifier using a classification algorithm, defined as a processes whereby a computing device 104 and/or any module and/or component operating thereon derives a classifier from training data 304. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to data of persons similar to human subject 116.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs as described in this disclosure as inputs, outputs as described in this disclosure as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 3, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 304.

Referring again to FIG. 2, and as a non-limiting example, computing device 104 may be configured to generate biometric signature by receiving subject signature training data 216, including a plurality of category descriptors and correlated physiological data entries, training a biometric signature model 220 as a function of the subject signature training data 216 and a machine-learning process, and generating the biometric identification signature 212 as a function of the biometric signature model 220. Training data may be collected by capturing a plurality of sensor readings having a categories matching categories of remote sensor 204 readings, which may, as a non-limiting example, be labeled by user 120 and/or category, for use in machine-learning process. Machine-learning process may identify one or more patterns of physiological data that are sufficiently unique to user 120 to be used as biometric identification signature 212.

Further referring to FIG. 2, computing device 104 may be configured to generate at least a biometric identification signature 212 by detecting highly divergent categories of data. As used in this disclosure, a "highly divergent category of data" is data that has a low degree of similarity from one user 120 to another, for instance and without limitation as measured according to a distance metric designed to evaluate similarity. As a non-limiting example, computing device 104 may receive a plurality of physiological data corresponding to a plurality of user 120s; plurality of data may be received and/or collected, without limitation, as described above for training data used to train biometric signature model 220, and may be labeled according to category and user 120. Computing device 104 may perform a feature learning algorithm on the plurality of physiological data. A "feature learning algorithm," as used herein, is a machine-learning algorithm that identifies associations between elements of data in a data set, which may include without limitation a training data set, where particular outputs and/or inputs are not specified. For instance, and without limitation, a feature learning algorithm 224 may detect co-occurrences of sets of physiological data, as defined above, with each other. As a non-limiting example, feature learning algorithm 224 may detect co-occurrences of gene combinations, as defined above, with each other. Computing device 104 may perform a feature learning algorithm 224 by dividing physiological data from a given person into various sub-combinations of such data to create physiological data sets as described above, and evaluate which physiological data sets tend to co-occur with which other physiological data sets; for instance, where physiological state data includes genetic sequences, computing device 104 may divide each genetic sequence into individual genes and evaluate which individual genes and/or combinations thereof tend to co-occur with which other individual genes, and/or other physiological data. In an embodiment, first feature learning algorithm 224 may perform clustering of data.

Continuing refer to FIG. 2, a feature learning and/or clustering algorithm may be implemented, as a non-limiting example, using a k-means clustering algorithm. A "k-means clustering algorithm" as used in this disclosure, includes cluster analysis that partitions n observations or unclassified cluster data entries into k clusters in which each observation or unclassified cluster data entry belongs to the cluster with the nearest mean, using, for instance behavioral training set as described above. "Cluster analysis" as used in this disclosure, includes grouping a set of observations or data entries in way that observations or data entries in the same group or cluster are more similar to each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. Cluster analysis may include hard clustering whereby each observation or unclassified cluster data entry belongs to a cluster or not. Cluster analysis may include soft clustering or fuzzy clustering whereby each observation or unclassified cluster data entry belongs to each cluster to a certain degree such as for example a likelihood of belonging to a cluster; for instance, and without limitation, a fuzzy clustering algorithm may be used to identify clustering of gene combinations with multiple disease states, and vice versa. Cluster analysis may include strict partitioning clustering whereby each observation or unclassified cluster data entry belongs to exactly one cluster. Cluster analysis may include strict partitioning clustering with outliers whereby observations or unclassified cluster data entries may belong to no cluster and may be considered outliers. Cluster analysis may include overlapping clustering whereby observations or unclassified cluster data entries may belong to more than one cluster. Cluster analysis may include hierarchical clustering whereby observations or unclassified cluster data entries that belong to a child cluster also belong to a parent cluster.

With continued reference to FIG. 2, computing device 104 may generate a k-means clustering algorithm receiving unclassified physiological state data and outputs a definite number of classified data entry clusters wherein the data entry clusters each contain cluster data entries. K-means algorithm may select a specific number of groups or clusters to output, identified by a variable "k." Generating a k-means clustering algorithm includes assigning inputs containing unclassified data to a "k-group" or "k-cluster" based on feature similarity. Centroids of k-groups or k-clusters may be utilized to generate classified data entry cluster. K-means clustering algorithm may select and/or be provided "k" variable by calculating k-means clustering algorithm for a range of k values and comparing results. K-means clustering algorithm may compare results across different values of k as the mean distance between cluster data entries and cluster centroid. K-means clustering algorithm may calculate mean distance to a centroid as a function of k value, and the location of where the rate of decrease starts to sharply shift, this may be utilized to select a k value. Centroids of k-groups or k-cluster include a collection of feature values which are utilized to classify data entry clusters containing cluster data entries. K-means clustering algorithm may act to identify clusters of closely related physiological data, which may be provided with user 120 cohort labels; this may, for instance, generate an initial set of user 120 cohort labels from an initial set of user 120 physiological data of a large number of user 120s, and may also, upon subsequent iterations, identify new clusters to be provided new user 120 cohort labels, to which additional user 120 physiological data may be classified, or to which previously used user 120 physiological data may be reclassified.

With continued reference to FIG. 2, generating a k-means clustering algorithm may include generating initial estimates for k centroids which may be randomly generated or randomly selected from unclassified data input. K centroids may be utilized to define one or more clusters. K-means clustering algorithm may assign unclassified data to one or more k-centroids based on the squared Euclidean distance by first performing a data assigned step of unclassified data. K-means clustering algorithm may assign unclassified data to its nearest centroid based on the collection of centroids ci of centroids in set C. Unclassified data may be assigned to a cluster based on $\text{argmin}_{ci \ni c} \text{dist}(ci, x)^2$, where argmin includes argument of the minimum, ci includes a collection of centroids in a set C, and dist includes standard Euclidean distance. K-means clustering module may then recompute centroids by taking mean of all cluster data entries assigned to a centroid's cluster. This may be calculated based on $ci=1/|Si|\Sigma xi \ni Si^{xi}$. K-means clustering algorithm may continue to repeat these calculations until a stopping criterion has been satisfied such as when cluster data entries do not change clusters, the sum of the distances have been minimized, and/or some maximum number of iterations has been reached.

Still referring to FIG. 2, k-means clustering algorithm may be configured to calculate a degree of similarity index value. A "degree of similarity index value" as used in this disclosure, includes a distance measurement indicating a measurement between each data entry cluster generated by k-means clustering algorithm and a selected physiological data set. Degree of similarity index value may indicate how close a particular combination of genes, negative behaviors and/or negative behavioral propensities is to being classified by k-means algorithm to a particular cluster. K-means clustering algorithm may evaluate the distances of the combination of genes, negative behaviors and/or negative behavioral propensities to the k-number of clusters output by k-means clustering algorithm. Short distances between a set of physiological data and a cluster may indicate a higher degree of similarity between the set of physiological data and a particular cluster. Longer distances between a set of physiological behavior and a cluster may indicate a lower degree of similarity between a physiological data set and a particular cluster.

With continued reference to FIG. 2, k-means clustering algorithm selects a classified data entry cluster as a function of the degree of similarity index value. In an embodiment, k-means clustering algorithm may select a classified data entry cluster with the smallest degree of similarity index value indicating a high degree of similarity between a physiological data set and the data entry cluster. Alternatively or additionally k-means clustering algorithm may select a plurality of clusters having low degree of similarity index values to physiological data sets, indicative of greater degrees of similarity. Degree of similarity index values may be compared to a threshold number indicating a minimal degree of relatedness suitable for inclusion of a set of physiological data in a cluster, where degree of similarity indices a-n falling under the threshold number may be included as indicative of high degrees of relatedness. The above-described illustration of feature learning using k-means clustering is included for illustrative purposes only, and should not be construed as limiting potential implementation of feature learning algorithms 224; persons skilled in the art, upon reviewing the entirety of this disclosure, will be aware of various additional or alternative feature learning approaches that may be used consistently with this disclosure.

In an embodiment, computing device 104 may identify at least a highly divergent data category, as a function of the feature learning algorithm 224. For instance, and without limitation, computing device 104 may identify as highly divergent categories of data that are highly divergent under a distance metric and/or degree of similarity index used in the feature learning algorithm 224. Computing device 104 may then generate at least a biometric identification signature 212 as a function of at least a highly divergent data category; for instance, training data elements and/or inputs and/or outputs of biometric signature model 220 may be selected by computing device 104 for categories of data matching highly divergent data categories.

Still referring to FIG. 2, computing device 104 is configured to determine a degree of similarity between plurality of current physiological data 208 and at least a biometric signature. A "degree of similarity," as used in this disclosure, is a measure of probability that a given set of data matches at least a biometric signature. Computing device 104 may, as a non-limiting example, determine the degree of similarity generating an error function of the plurality of current physiological data 208 and the at least a biometric signature, where error function may be any error function suitable for use in machine-learning processes as described above in reference to FIG. 3. Computing device 104 may determine degree of similarity as a function of the generating, for instance by setting a maximal recorded error function as corresponding to a 0% probability of a match, an error function of 0 as indicative of a 100% probability of a match, and calculating probabilities for intervening values accordingly.

Alternatively or additionally, computing device 104 may be configured to determine degree of similarity by generating a distance metric between the plurality of physiological data and the at least a biometric signature, and determining the degree of similarity as a function of the distance metric, for instance by setting a maximal recorded distance metric as corresponding to a 0% probability of a match, an distance metric of 0 as indicative of a 100% probability of a match, and calculating probabilities for intervening values accordingly. A "distance metric," as used in this disclosure, is a quantitative value indicating a degree of similarity of a set of data values to another set of data values. For instance, and without limitation, data of a biometric identification signature 212 and current physiological data 208 being compared thereto may each be represented as vectors. Each vector may be represented, without limitation, as an n-tuple of values, where n is at least two values. Each value of n-tuple of values may represent a measurement or other quantitative value associated with a given category of data, or attribute, such as a nutrients, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. A non-limiting distance metric may include a degree of vector similarity. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent, for instance as measured using cosine similarity; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute 1 as derived using a Pythagorean norm: $l=\sqrt{\Sigma_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Further referring to FIG. 2, computing device 104 may be configured to calculate an identity quantifier 228 as a function of the degree of similarity. An "identity quantifier," as used in this disclosure, is a quantitative value that measures probability that current physiological data 208 matches to human subject 116. Identity quantifier 228 may include a single degree of similarity as calculated above, and/or two or more identity quantifiers 228 aggregated together using methods of aggregation such as averaging, adding, or the like. For instance, and without limitation, computing device 104 may iteratively and/or periodically determine degrees of similarity, aggregating each newly generated degree of similarity to identity quantifier 228 to form a "running total"; this may be performed throughout a telemedicine session as a form of periodic and/or continuous authentication of current physiological data 208.

Still referring to FIG. 2, computing device 104 may be configured to authenticate a physiological sample set as a function of the identity quantifier 228. As used in this disclosure, a "physiological sample set" is a set of physiological data, which may include any data suitable for use as current physiological data 208 as described above, that is used for medical evaluation, diagnosis, or other purposes by a user 120 conducting telemedicine using system 100. "Authentication," as used in this disclosure, is a verification that physiological sample set may be treated as originating at human subject 116 rather than at another person. Authentication may include comparison of identity quantifier 228 to a threshold number, which may be a preconfigured number representing an acceptable level of probability that plurality of current physiological data 208 identifies human subject 116. Physiological sample set may include plurality of physiological data; for instance, data from physiological sample set may be used to determine a degree of similarity to biometric identification signature 212, which may then be used to generate an identity quantifier 228 to be used in authentication of physiological sample set. As a result, each set of data to be used as physiological sample set may be authenticated biometrically, ensuring that it originates from human subject 116, and/or all such data may be used to continuously and/or periodically authenticate identity of human subject 116 throughout a telemedicine session. Alternatively or additionally, physiological sample set may be a separate set of data from current physiological data 208, which may be captured concurrently with current physiological data 208 using the same channel or a separate channel; for instance, system 100 may periodically analyze voice, facial features, fingerprint, and/or motion of human subject 116 at the same time physiological sample set is being captured.

Still referring to FIG. 2, computing device 104 is configured to provide plurality of current physiological data to user 120 of computing device 104 as a function of identity quantifier. Provision may include provision with identity quantifier; in other words, computing device 104 may display identity quantifier with current physiological data, for instance as a number, a color code, or the like. Color code may include without limitation a first color indicative of a high probability of association of physiological data with biometric identifier, a second color indicative of a lower probability of association of physiological data with biometric identifier, and/or a third color indicative of a still lower probability of association of physiological data with biometric identifier; these colors may, as a non-limiting example, be green, yellow, and red, respectively. More gradations of colors and/or different color choices may alternatively be employed. As a further non-limiting example, physiological data may be provided only if authenticated as described above; in other words, a user 120 of computing device 104 may be able to utilize physiological data only if it sufficiently matches biometric signature as described above.

Further referring to FIG. 2, current physiological data and/or physiological sample set may be used in one or more additional prognostic, diagnostic, or other medical analytical processes. Diagnostic procedures may be performed, without limitation, as described in U.S. Nonprovisional application Ser. No. 16/372,512, filed on Apr. 2, 2019, and entitled "METHODS AND SYSTEM 100S FOR UTILIZING DIAGNOSTICS FOR INFORMED VIBRANT CONSTITUTIONAL GUIDANCE," the entirety of which is incorporated herein by reference.

Still referring to FIG. 2, any determination performed with regard to biometric signature, including without limitation authentication as described above, may be used for purposes of establishing a security baseline and/or detecting changes thereto as described in U.S. Nonprovisional application Ser. No. 16/919,674, filed on Jul. 2, 2020, and entitled "METHODS AND SYSTEM 100S FOR GENERATING A SECURE COMMUNICATION CHANNEL INTERFACE 108 FOR STREAMING OF SENSITIVE CONTENT," the entirety of which is incorporated herein by reference.

Figure 4:
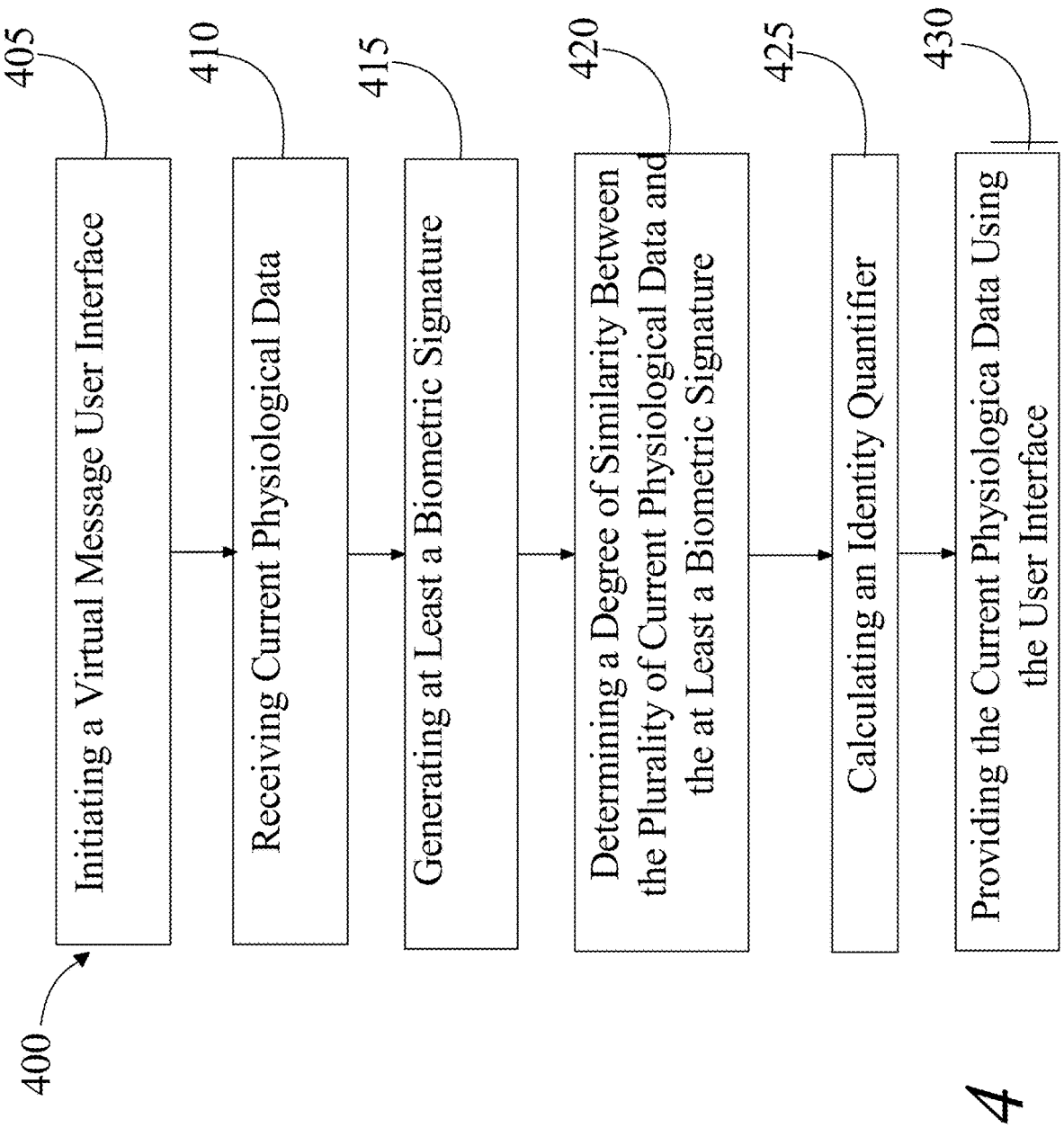
FIG. 4 is a flow diagram of an exemplary embodiment of a method of biometric identification in telemedicine using remote sensing.

Referring now to FIG. 4, an exemplary embodiment of a method 400 of biometric identification in telemedicine using remote sensing is illustrated. At step 405, a computing device 104 initiates a communication interface between the computing device 104 and a client device 112 operated by a human subject 116, wherein the communication interface includes an audiovisual streaming protocol; this may be implemented, without limitation, as described above in reference to FIGS. 1-3.

At step 410, and still referring to FIG. 4, computing device 104 receives, from at least a remote sensor 204 at the human subject 116, a plurality of current physiological data 208; this may be implemented, without limitation, as described above in reference to FIGS. 1-3. For instance, and without limitation, plurality of current physiological data 208 may include heart rate data, motion detector data, image data, and/or audio data.

At step 415, and with further reference to FIG. 4, computing device 104s generates at least a biometric identification signature 212 of the human subject 116; this may be implemented, without limitation, as described above in reference to FIGS. 1-3. Generating includes receiving subject signature training data 216, including a plurality of category descriptors and correlated physiological data entries, training a biometric signature model 220 as a function of the subject signature training data 216 and a machine-learning process, and generating the biometric identification signature 212 as a function of the biometric signature module.

At step 420, computing device 104 determines a degree of similarity between the plurality of current physiological data 208 and the at least a biometric signature; this may be implemented, without limitation, as described above in reference to FIGS. 1-3.

At step 425, computing device 104 calculates an identity quantifier 228 as a function of the degree of similarity; this may be implemented, without limitation, as described above in reference to FIGS. 1-3.

At step 430, computing device 104 provides plurality of current physiological data 208 to a user 120 of computing device 104 using the communication interface; this may be implemented, without limitation, as described above in reference to FIGS. 1-3.

Figure 5:
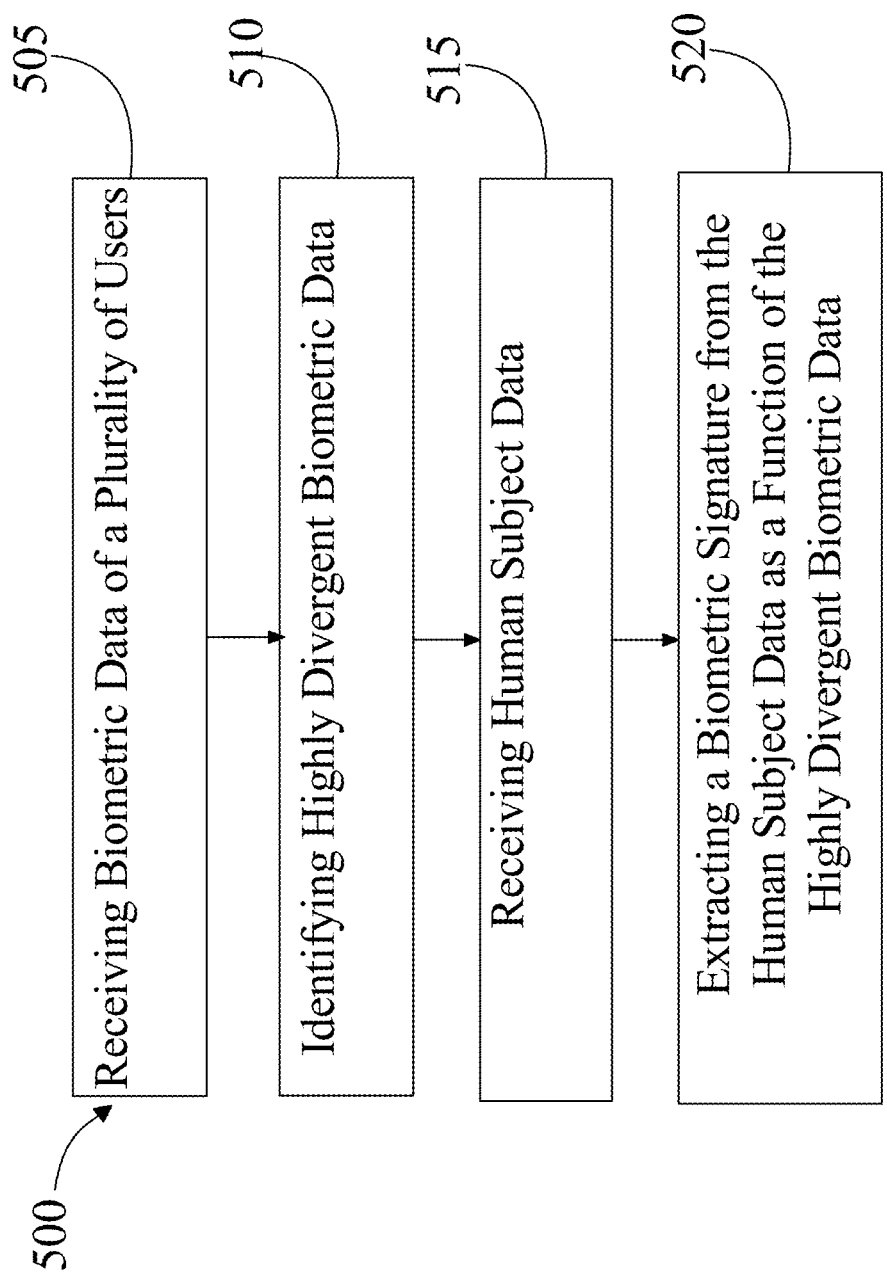
FIG. 5 is a flow diagram of an exemplary embodiment of a method of extraction of biometric signatures.

Referring now to FIG. 5, an exemplary embodiment of a method 500 of extracting a biometric signature of a human subject 116 is illustrated. At step 505, biometric data of a plurality of user 120s is received; this may be implemented, without limitation, as described above in reference to FIGS. 1-3.

At step 510, and still referring to FIG. 5, a computing device 104 identifies highly divergent biometric data as a function of the biometric data of the plurality of user 120s; this may be implemented, without limitation, as described above in reference to FIGS. 1-3. For instance, and without limitation, computing device 104 may identify the highly divergent biometric data using a feature learning algorithm as described above.

At step 515, computing device 104 receives human subject 116 data, which may include without limitation current clinical measurement data; this may be implemented, without limitation, as described above in reference to FIGS. 1-3.

At step 520, computing device 104 extracts a biometric signature from human subject 116 data as a function of the highly divergent biometric data; this may be implemented, without limitation, as described above in reference to FIGS. 1-3.

It is to be noted that any one or more of the aspects and embodiments described herein may be conveniently implemented using one or more machines (e.g., one or more computing devices that are utilized as a user 120 computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
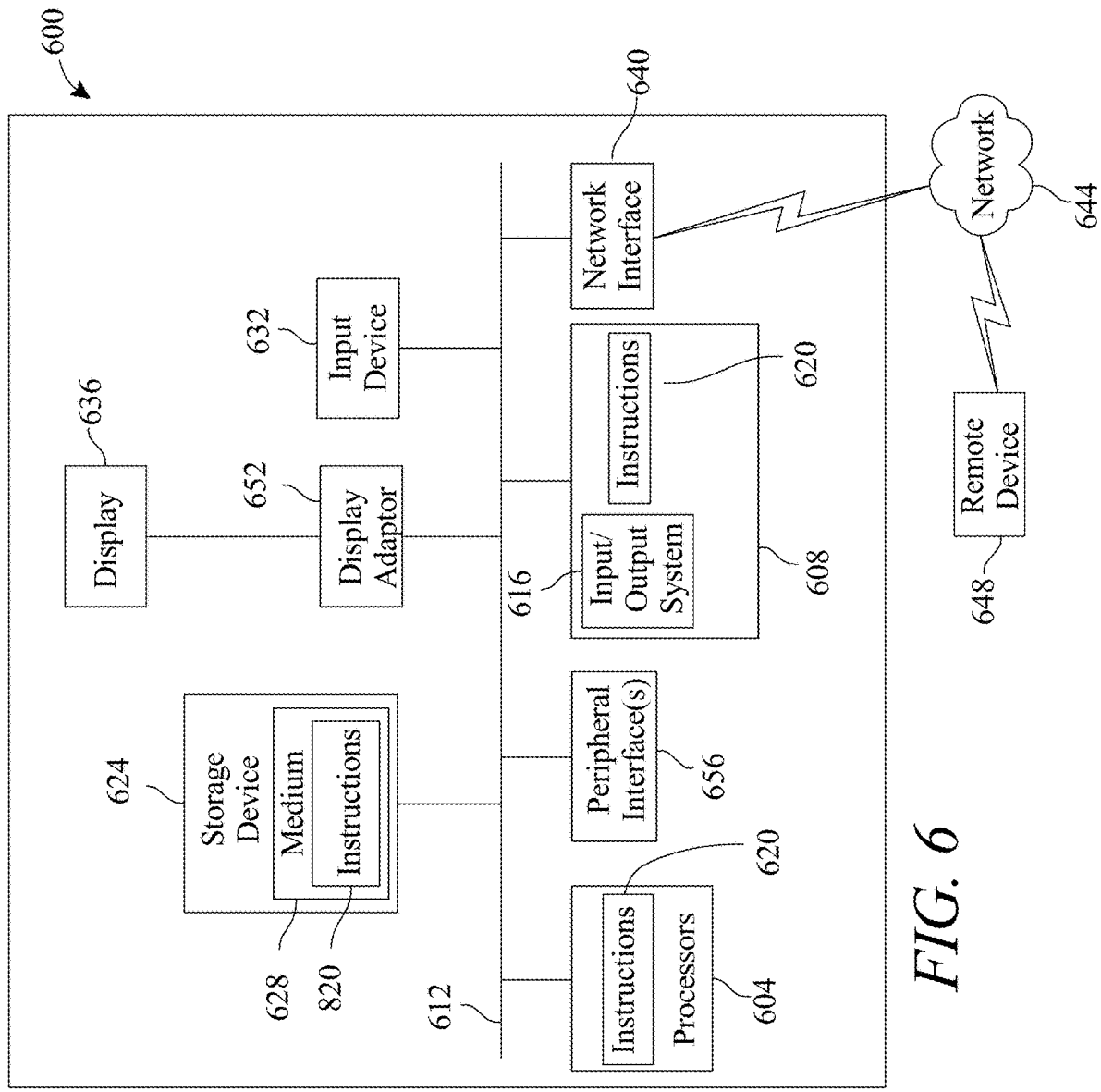
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 100 600 within which a set of instructions for causing a control system 100 to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 100 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Processor 604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system 100 on a chip (SoC)

Memory 608 may include various components (e.g., machine-readable media) including, but not limited to, a random-access memory component, a read only component, and any combinations thereof. In one example, a basic input/output system 100 616 (BIOS), including basic routines that help to transfer information between elements within computer system 100 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system 100, one or more application programs, other program modules, program data, and any combinations thereof.

Computer system 100 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 100 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 100 600. In one example, software 620 may reside, completely or partially, within machine-readable medium 628. In another example, software 620 may reside, completely or partially, within processor 604.

Computer system 100 600 may also include an input device 632. In one example, a user 120 of computer system 100 600 may enter commands and/or other information into computer system 100 600 via input device 632. Examples of an input device 632 include, but are not limited to, an alpha-numeric input device (e.g., a keyboard), a pointing device, a joystick, a gamepad, an audio input device (e.g., a microphone, a voice response system 100, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user 120 selection device for selecting one or more graphical representations in a graphical interface as described above.

A user 120 may also input commands and/or other information to computer system 100 600 via storage device 624 (e.g., a removable disk drive, a flash drive, etc.) and/or network interface device 640. A network interface device, such as network interface device 640, may be utilized for connecting computer system 100 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 100 600 via network interface device 640.

Computer system 100 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 100 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, system 100s, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:
1. A system for biometric identification in telemedicine using remote sensing, the system comprising:
    a computing device at a first location, the computing device configured to:
    initiate a communication interface between the computing device and a client device associated with a human subject and at a second location, wherein the communication interface includes an audiovisual streaming protocol;
receive, from at least a remote sensor at the human subject, a plurality of current physiological data associated with the human subject;
generate at least a biometric identification signature of the human subject, wherein generating further comprises:
receiving a subject signature training data, wherein the subject signature training data correlates a plurality of category descriptors and physiological data entries;
training a biometric signature model as a function of a machine-learning process, wherein the machine-learning process is trained as a function of the subject signature training data; and
generating the biometric identification signature as a function of the biometric signature model;
determine a degree of similarity between the plurality of current physiological data and the at least a biometric signature, wherein the degree of similarity measures a probability as a function an error function;
calculate an identity quantifier as a function of the degree of similarity; and
provide the plurality of physiological data to a user of the computing device using the communication interface.

2. The system of claim 1, wherein the plurality of current physiological data further comprises heart rate data.

3. The system of claim 1, wherein the plurality of current physiological data further comprises motion detector data.

4. The system of claim 1, wherein the plurality of current physiological data further comprises image data.

5. The system of claim 1, wherein the plurality of current physiological data further comprises audio data.

6. The system of claim 1, wherein the computing device is further configured to generate the at least a biometric identification signature by:
receiving a plurality of physiological data corresponding to a plurality of users;
performing a feature learning algorithm on the plurality of physiological data;
identifying, as a function of the feature learning algorithm, at least a highly divergent data category; and
generating the at least a biometric identification signature as a function of the at least a highly divergent data category.

7. The system of claim 1, wherein the computing device is further configured to determine the degree of similarity by:
generating an error function of the plurality of current physiological data and the at least a biometric signature; and
determining the degree of similarity as a function of the generating.

8. The system of claim 1, wherein the computing device is further configured to determine the degree of similarity by:
generating a distance metric between the plurality of physiological data and the at least a biometric signature; and
determining the degree of similarity as a function of the distance metric.

9. The system of claim 1, wherein the computing device is configured to authenticate a physiological sample set as a function of the identity quantifier.

10. The system of claim 9, wherein the physiological sample set includes the plurality of physiological data.

11. A method of biometric identification in telemedicine using remote sensing, the method comprising:
initiating, by a computing device at a first location, a communication interface between the computing device and a client device associated with a human subject and at a second location, wherein the communication interface includes an audiovisual streaming protocol;
receiving, by the computing device and from at least a remote sensor at the human subject, a plurality of current physiological data;
generate, by the computing device, at least a biometric identification signature of the human subject, wherein generating further comprises:
receiving a subject signature training data, wherein the subject signature training data correlates a plurality of category descriptors and physiological data entries;
training a biometric signature model as a function of a machine-learning process, wherein the machine-learning process is trained as a function of the subject signature training data; and
generating the biometric identification signature as a function of the biometric signature module;
determining, by the computing device, a degree of similarity between the plurality of current physiological data and the at least a biometric, wherein the degree of similarity measures a probability as a function an error function;
calculating, by the computing device, an identity quantifier as a function of the degree of similarity; and
providing the plurality of physiological data to a user of the computing device using the communication interface.

12. The method of claim 11, wherein the plurality of current physiological data further comprises heart rate data.

13. The method of claim 11, wherein the plurality of current physiological data further comprises motion detector data.

14. The method of claim 11, wherein the plurality of current physiological data further comprises image data.

15. The method of claim 11, wherein the plurality of current physiological data further comprises audio data.

16. The method of claim 11, wherein generating the at least a biometric identification signature further comprises:
receiving a plurality of physiological data corresponding to a plurality of users;
performing a feature learning algorithm on the plurality of physiological data;
identifying, as a function of the feature learning algorithm, at least a highly divergent data category; and
generating the at least a biometric identification signature as a function of the at least a highly divergent data category.

17. The method of claim 11, wherein determining the degree of similarity further comprises:
generating an error function of the plurality of current physiological data and the at least a biometric signature; and
determining the degree of similarity as a function of the generating.

18. The method of claim 11, wherein determining the degree of similarity further comprises:
generating a distance metric between the plurality of physiological data and the at least a biometric signature; and determining the degree of similarity as a function of the distance metric.

19. The method of claim 11 further comprising authenticating a physiological sample set as a function of the identity quantifier.

20. The method of claim 19, wherein the physiological sample set includes the plurality of physiological data.

\* \* \* \* \*